United States Patent [19]

Bott et al.

[11] Patent Number: 5,763,665

[45] Date of Patent: Jun. 9, 1998

[54] PREPARATION OF CRYSTALLINE N-METHYLOL-(METH) ACRYLAMIDE

[75] Inventors: Kaspar Bott, Mannheim; Thomas Domschke, Speyer; Michael Bohn, Ludwigshafen, all of Germany

[73] Assignee: BASF Aktiengesellschaft, Ludwigshafen, Germany

[21] Appl. No.: 765,214

[22] PCT Filed: Jul. 5, 1995

[86] PCT No.: PCT/EP95/02594

§ 371 Date: Jan. 3, 1997

§ 102(e) Date: Jan. 3, 1997

[87] PCT Pub. No.: WO96/01251

PCT Pub. Date: Jan. 18, 1996

[30] Foreign Application Priority Data

Jul. 6, 1994 [DE] Germany ............... 44 23 740.5

[51] Int. Cl.⁶ .................................................. C07C 209/02
[52] U.S. Cl. ........................................ 564/408; 564/404
[58] Field of Search ............................... 564/208, 204

[56] References Cited

U.S. PATENT DOCUMENTS

| | | | |
|---|---|---|---|
| 2,864,861 | 12/1958 | Wohnseidler et al. | 260/561 |
| 2,864,862 | 12/1958 | Sutherland | 260/561 |
| 3,064,050 | 11/1962 | Saunders | 260/561 |
| 3,898,279 | 8/1975 | Hoke | 260/561 N |
| 5,220,065 | 6/1993 | Takayanagi et al. | 564/208 |

*Primary Examiner*—Brian M. Burn
*Attorney, Agent, or Firm*—Keil & Weinkauf

[57] ABSTRACT

In a process for the preparation of crystalline N-methylol (meth)acrylamide from (meth)acryamide and paraformaldehyde, the reaction of the solid reactants to give a product melt and the subsequent crystallization thereof in a reactor while subjecting the reaction mixture to mechanical shear load is preferably carried out in a self-purging screw reactor or a disk reactor. The reaction of the reactants and the crystallization of the product melt are preferably carried out without added solvent. A catalyst, in particular an alkali metal carbonate or a trialkylamine, can be used for the reaction of the reactants.

10 Claims, 1 Drawing Sheet

PREPARATION OF CRYSTALLINE N-METHYLOL-(METH) ACRYLAMIDE

This application is a 35 U.S.C. 371 of PCT/EP95/02594, filed Jul. 5, 1995.

The present invention relates to a process for the preparation of crystalline N-methylol(meth)acrylamide from paraformaldehyde and (meth)acrylamide in the presence of a suitable catalyst.

N-Methylol(meth)acrylamide is used as a monomer component with crosslinking properties in a number of polymers, predominantly in polymer emulsions, which are used as adhesives and coating materials, as binders for paints and fibers and as material for textile or paper coating.

Processes for the preparation of crystalline N-methylolacrylamide are known. Thus, U.S. Pat. No. 3,064,050 describes such a process in which acrylamide and paraformaldehyde in highly concentrated aqueous solution are reacted using a basic catalyst. The disadvantages of this process are a) the relatively low product yields of about 50% which are obtained in one operation, b) the recycling of the mother liquors which is therefore required and c) the drying of the product obtained by filtration.

U.S. Pat. No. 2,864,861 discloses a process for obtaining N-methylolacrylamide which dispenses with the use of any solvents. In this known process, a product melt is produced in a stirred kettle from the solid reactants paraformaldehyde and acrylamide using a catalytic amount of triethylamine and is allowed to solidify to solid N-methylolacrylamide after the end of the reaction by cooling. If this process were scaled up to a large industrial plant, it would not be possible to achieve the following:

a) to mix the reactants uniformly;

b) to remove the heat of reaction rapidly in order to avoid an b) to remove the heat of reaction rapidly in order to avoid an accumulation of heat and hence the danger of polymerization;

c) to produce an N-methylolacrylamide of constant quality and d) to discharge the N-methylolacrylamide in free-flowing form from the stirred kettle.

It is an object of the present invention to provide a solvent-free process for the preparation of N-methylol (meth)acrylamide in which the abovementioned features are also achievable on the large industrial scale.

We have found that this object is achieved, according to the invention, by the processes defined in the claims. In particular, (meth)acrylamide and paraformaldehyde are reacted using a suitable catalyst in one process step to give crystalline N-methylol(meth)acrylamide by carrying out the reaction in a reactor, preferably in a self-purging screw apparatus. The reactor is designed in such a way that the reaction mixture is exposed to significant shear loads, as in screw extruders or in disk mixers. These apparatuses are known per se, and the degree or the intensity of mechanical mixing for the reaction and the crystallization is therefore also defined. Preferably used reactors are those which transmit to the reaction mixture a shear load which, based on the power consumption per unit volume of content, is of the same order to magnitude as that of the commercial apparatuses stated in the Examples, the material contained being the same.

Below, (meth)acrylamide is to be understood as meaning acrylamide and/or methacrylamide. Suitable catalysts are tertiary amines or alkali metal carbonates, in particular potassium carbonate. This process, which can be operated by either a continuous or batchwise procedure, gives a free-flowing product with small quality fluctuations. The mode of operation of the Discotherm B used for carrying out the present process will be described in detail below:

Highly self-purging reactors are preferably used for the preparation of N-methylol(meth)acrylamide. Such a reactor is, for example, a Discotherm B from List AG, 4422 Arisdorf, Switzerland, in which the required residence time can be realized.

The Discotherm B (DTB) is a batchwise or continuous kneading apparatus. It consists of a horizontal cylindrical barrel with a concentric stirring shaft on which disk elements are mounted in planes at right angles to the axis and kneader-mixer bars on the outer circumference. Static counter-hooks which clean the shaft and the disk elements are fastened in the barrel. The degree of self-purging of the apparatus is 90%. The remaining 10% are purged by means of product movements. The axial transport is ensured by the arrangement of the disk elements with kneader-mixer bars and by the shape of the counter-hooks. Axial mixing is small, so that a narrow residence time range can be realized. The barrel, shaft and disk elements are heatable and coolable. The degree of filling (preferably 60–80%) can be set by means of the height of an adjustable overflow weir at the apparatus discharge.

EXAMPLE 1

Batchwise preparation of N-methylolacrylamide

Figure 1:
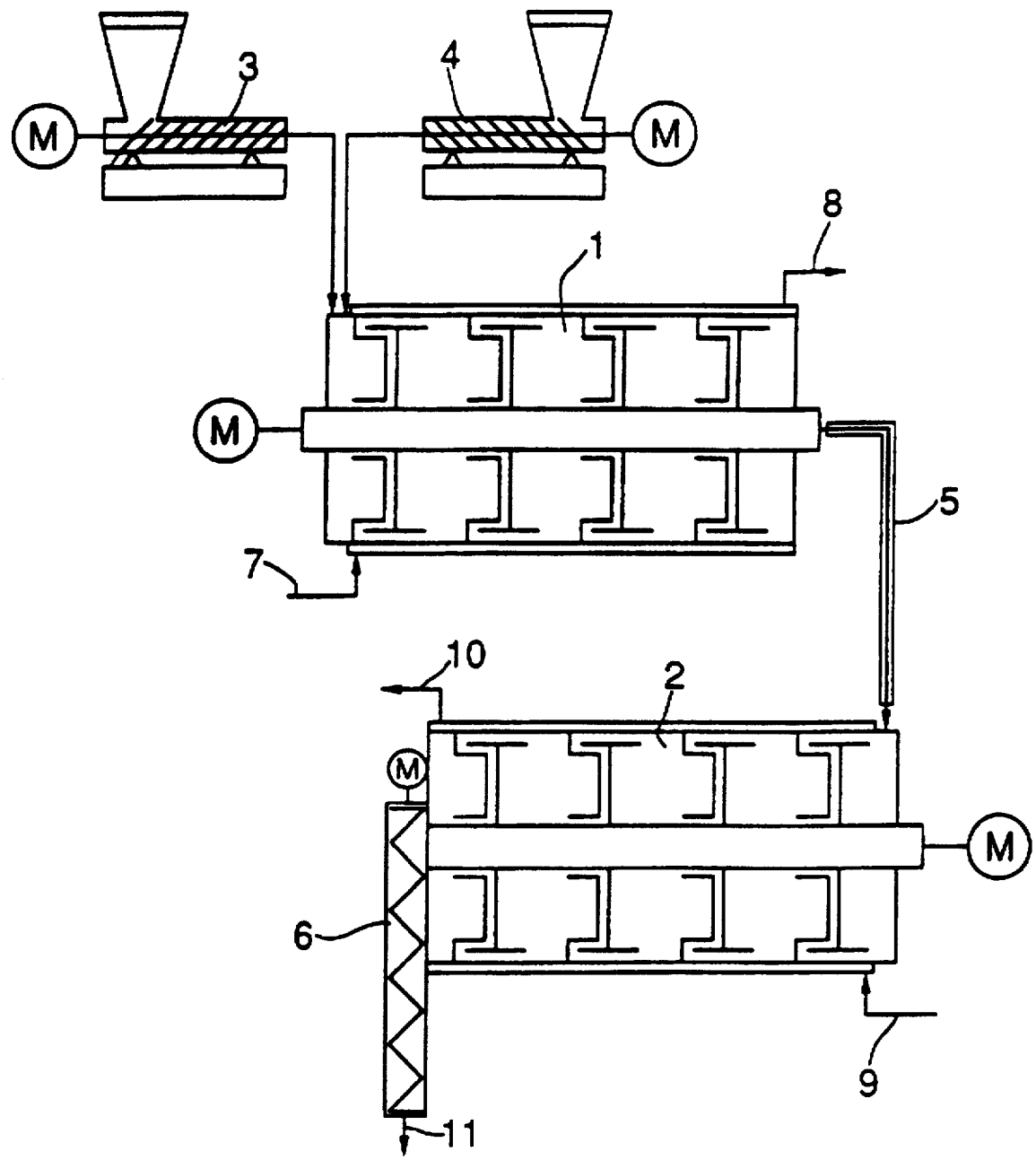
FIG. 1 depicts an apparatus which may be used with a preferred embodiment of the invention (see Example 2). "M" denotes various drive units. "1" denotes a first reactor and "2" denotes a second reactor. "3" and "4" denote differential metering balances which may aid in metering reactant and catalyst to the first reactor 1. "5" denotes a pipeline which allows flow of product from the first reactor 1 to the second reactor 2. "6" denotes a vertical conveying screw used to continuously discharge product from the second reactor 2. "7" depicts a pipe used to bring heating water to the first reactor 1 and "8" depicts a pipe for removing the heating water from the first reactor 1. Similarly, "9" depicts a pipe used to bring cooling water to the second reactor 2 and "10" depicts a pipe for removing the cooling water from the second reactor 2. "11" depicts a pipe used to channel the flow of product from the conveying screw 6.

The starting materials acrylamide, paraformaldehyde and potassium carbonate are in the form of free-flowing powders. 13.78 kg of acrylamide, 6.12 kg of paraformaldehyde and 0.1 kg of potassium carbonate are introduced into a Discotherm B, type designation DTB-40-Batch (free volume about 60 l), and are mixed at a speed of 50 min$^{-1}$. The reactor is heated to 50° C. After about 30 minutes, the reaction is complete and the N-methylolacrylamide is in the form of a clear melt. The reactor is then cooled to about 20° C. so that the N-methylol-acrylamide melt begins to crystallize. After a cooling time of 45 minutes, the N-methylolacrylamide has completely crystallized out and is discharged from the reactor in the form of a fine-grained powder. The product obtained has a melting point of 53°–57° C.

EXAMPLE 2

Continuous preparation of N-methylolacrylamide

The structure of the apparatus is shown in the Figure. The various drive units are denoted there in general by M. 20.67 kg/h of acrylamide, 9.18 kg/h of paraformaldehyde and 0.15 kg/h of potassium carbonate are metered continuously into the reactor 1 of the type Discotherm B (DTB 40-Conti) with the aid of two differential metering balances 3 and 4 of the type K-Tron Soder (total throughput 30 kg/h). Paraformaldehyde and potassium carbonate are metered in as a mixture. The reactor 1 is heated by hot water (50° C.) which flows in through the pipe 7 and flows away again through pipe 8. The shaft speed is 50 min$^{-1}$. At a degree of filling of about 60% and a residence time of >35 min, the solids react to give a clear melt, which flows, under the influence of gravity, continuously through a pipeline 5 heated to 50° C. with hot water into the second reactor 2. The second reactor 2 is likewise a DTB 40-Conti which is thermostated at 20° C. by cooling water flowing in through the pipe 9 and flowing away through pipe 10, so that the melt crystallizes. At a shaft speed of 25 min$^{-1}$, a degree of filling of 60% and a residence time of >35 min, a fine-grained solid is obtained at the end of the reactor and is discharged continuously via the pipe 11 by means of a vertical conveying screw 6.

We claim:

1. A process for the preparation of crystalline N-methylol (meth)acrylamide comprising:

A) reacting a mixture of (meth)acrylamide and paraformaldehyde by subjecting the mixture to a mechanical shear load in a reactor, thereby producing a product melt; and B) crystallizing said product melt.

2. The process of claim 1, wherein the reaction of the reactants and the crystallization of the product melt are carried out without the addition of solvent.

3. The process of claim 1, wherein a catalyst is added to the mixture.

4. The process of claim 3, wherein the catalyst is selected from the group consisting of an alkali metal carbonate and a trialkylamine.

5. The process of claim 1, wherein the reaction is carried out in a self-purging screw reactor or a disk reactor.

6. The process of claim 5, wherein the reaction is carried out in a twin-screw extruder having screws rotating in the same direction.

7. The process of claim 1, wherein the reaction mixture is exposed to the shear load in a first section of the reactor, and crystallization takes place in a second section.

8. The process of claim 7 wherein said first and second sections of the reactor have shear load means which can be regulated independently of one another.

9. The process of claim 1, wherein the process is carried out by a continuous method.

10. The process of claim 9, wherein a narrow residence time range for the mixture in the reaction is maintained.

* * * * *